United States Patent [19]

Trainer

[11] Patent Number: 5,416,580
[45] Date of Patent: May 16, 1995

[54] METHODS AND APPARATUS FOR DETERMINING SMALL PARTICLE SIZE DISTRIBUTION UTILIZING MULTIPLE LIGHT BEAMS

[75] Inventor: Michael N. Trainer, Telford, Pa.

[73] Assignee: General Signal Corporation

[21] Appl. No.: 88,445

[22] Filed: Jul. 7, 1993

[51] Int. Cl.⁶ .............................................. G01N 15/02
[52] U.S. Cl. ..................................... 356/336; 356/343
[58] Field of Search ............... 356/336, 338, 340, 343; 250/574

[56] References Cited

U.S. PATENT DOCUMENTS 5,280,272  1/1994  Nagashima et al. ................. 356/340

FOREIGN PATENT DOCUMENTS 0559529  9/1993  France .

OTHER PUBLICATIONS

Cilas 1064. "The high resolution particle size analyzer" brochure from Cilas.

Primary Examiner—Richard A. Rosenberger
Attorney, Agent, or Firm—Joseph J. Kaliko

[57] ABSTRACT

A method (and corresponding apparatus) for determining the size distribution of small particles within a dispersing medium utilizing a particle analyzer that measures the angle of scattered light, including the step of sequentially irradiating the particles within the dispersing medium with each of a plurality of light sources positioned at different angles. The scattered light developed by sequentially irradiating the particles is focused, utilizing at least one collector lens, onto a detector array associated with each such lens and the angular distribution of scattered light associated with each of the plurality of light sources is sequentially measured utilizing each detector array associated with a given lens. Finally, the measured angular distributions of scattered light associated with the plurality of light sources, is translated into a size distribution for the particle ensemble contained in the dispersing medium, using well known inversion techniques, such as deconvolution. The invention also contemplates methods for extending the angular scatter measurement range of a particle size analyzers that use a single light source to irradiate particles, and products that are the result of the extension process.

21 Claims, 8 Drawing Sheets

(PRIOR ART)

FIG. 3

(PRIOR ART)

| LIGHT BEAM | SCATTERING ANGLE RANGE | |
|---|---|---|
| A | 0° | 40° |
| B | 30° | 80° |
| C | 80° | 130° |
| D | 120° | 170° |

METHODS AND APPARATUS FOR DETERMINING SMALL PARTICLE SIZE DISTRIBUTION UTILIZING MULTIPLE LIGHT BEAMS

BACKGROUND OF THE INVENTION

1. Field of the Invention

The invention relates generally to the field of determining particle size distributions, including volume distributions (particle volume per particle diameter interval); area distributions (particle area per particle diameter interval); and particle number distributions (particle number per particle diameter interval).

More particularly the invention relates to methods and apparatus for determining the size distribution of small particles using multiple light beams to extend the angular scatter measurement range of a particle size analyzer.

2. Description of the Related Art

Methods and apparatus are well known for determining the size distribution of particulate material for particles in the approximate range of 0.1 to 100 microns in diameter. For example, Wilcock, in U.S. Pat. No. 3,873,206, issued Mar. 25, 1975, and Wertheimer, in U.S. Pat. No. 4,134,679, issued Jan. 16, 1979, both assigned to the assignee of the present invention, describe such methods.

A further example of prior art for determining the size distribution of small particles is taught in U.S. Pat. No. 5,094,532, to Trainer et al., issued Mar. 10, 1992, also assigned to the assignee of the present invention. According to Trainer et al., a beam of light is directed into a scattering medium to measure the size distribution of particles experiencing Brownian motion.

In particular, according to Trainer et al., the frequency of the scattered light is compared with the frequency of the source light. The comparison results in the generation of a first signal having a frequency that varies with time and is indicative of the difference in the frequency between the scattered light and the source light. A second signal is generated having a magnitude which varies with frequency on a linear scale. The frequency scale is then translated to a logarithmic scale. Finally, the translated second signal is deconvolved to determine the size distribution of moving particles within the scattering medium.

Although scattered light frequency measurement is now a recognized technique for determining the size distribution of very small particles (less than 2 microns in diameter); most commercially available particle size distribution measuring systems (typically used to measure particles from 0.1 to 1000 microns in diameter), use the technique of analyzing the angular distribution of light scattered (from the particles) to determine particle size distribution. This is because as particle size increases the velocities of particles due to Brownian motion become too small to measure.

An example of a commercially available instrument that analyzes the angular distribution of light scattered from particles to determine particle size distribution is the Microtrac Standard Range Analyzer (SRA) manufactured by Leeds & Northrup Company ("Microtrac" is a registered trademark owned by Leeds & Northrup Company).

In the SRA a collimated monochromatic light beam irradiates an ensemble of particles flowing perpendicularly through the collimated beam. Light scattered from the particles emerges from the interaction volume at an angle from the axis of the collimated beam. The scattered light is collected by a lens placed in the path of the scattered light.

The scattered light pattern, focused in the focal plane of the lens, is typically measured by an array of photodetectors placed in the focal plane. The angular extent of the scatter pattern is determined by the size of the scattering particle. The smaller the particle, the wider the angular extent of the scatter; the larger the particle, the narrower the angular extent of scatter.

It is well known in the art that the scattered light from a mixture of different sized particles is simply the sum of all of the individual scattering distributions from each size, weighted by the total particle number at that size. The particle size distribution may be "inverted" from this composite scattering distribution by using well known mathematical algorithms, such as deconvolution.

In order to obtain good size resolution in the size distribution in a system that analyzes the angular distribution of light scattered (for example, the SRA), the scattered light bundles at each angle must be focused, with low optical aberration, to a small spot on the detector array. The scattering angle range of a single lens is limited by aberrations, such as distortion and field curvature, which increase with lens field angle.

For a typical system with a collector lens on the axis of the collimated beam (like the SRA), the angular range collected by the lens also depends upon the lens diameter and the distance from the sampling volume.

Because of the aforementioned factors, optical measuring systems like the SRA have an angular range limited to approximately 15 degrees. This results in a high resolution measurement capability extending down to only a few microns in particle diameter when using a 0.75 micron light source, typically a laser.

Those skilled in the art will recognize that extending the angular scatter measurement range of systems that analyze the angular distribution of light (to determine particle size distribution) has several benefits, including being able to increase the measurement capabilities of such systems to the submicron range; while at the same time being able to perform data collection in time frames that are typically shorter then would be required by the aforementioned light frequency measurement techniques.

In order to achieve these benefits, larger scattering angles have been measured using an off axis collector lens and a measurement photodiode detector array in the focal plane of the off axis lens. This arrangement has allowed the angular range to be extended out to about 50 degrees and a high resolution particle size determination to be extended down to approximately 0.4 microns.

An example of a commercially available instrument that analyzes the angular distribution of light using both an on axis and off axis collector lens (and their associated detector arrays), together with shared data processing equipment, is the Microtrac Full Range Analyzer (FRA) manufactured by Leeds & Northrup Company.

The further extension of the angular measurement range beyond the range achieved by using systems like the FRA, can be accomplished by adding more off axis collector lenses and photodetector arrays. However, this approach is problematic in that: (a) each lens and detector array set has to be aligned, calibrated and matched to the other lens/detector sets to measure a wider scatter pattern; and (b) since the lens angular field is limited by aberrations, many expensive lens/detector sets are needed to cover the large angular range required for measuring small particles using a single light source.

It should be noted that in addition to the aforementioned techniques for determining small particle size distributions, other techniques exist which make the desired determination utilizing (a) fringe patterns caused by the interference of at least two light beams or (b) particle counting techniques.

Exemplary fringe pattern oriented techniques are described in U.S. Pat. No. 4,179,218, to Erdmann et al., issued Dec. 18, 1979; U.S. Pat. No. 4,329,054, to Bachalo, issued May 11, 1982; U.S. Pat. No. 4,537,507, to Hess, issued Aug. 27, 1985; U.S. Pat. No. 4,596,036, to Norgren et al., issued Jun. 17, 1986; and U.S. Pat. No. 4,701,051, to Buchhave et al., issued Oct. 20, 1987.

Exemplary particle counting techniques are described in U.S. Pat. No. 4,251,733, to Hirleman, Jr., issued Feb. 17, 1981; U.S. Pat. No. 4,348,111, to Goulas et al., issued Sep. 7, 1982; U.S. Pat. No. 4,444,500, to Flinsenberg et al., issued Apr. 24, 1984; and U.S. Pat. No. 4,957,363, to Takeda et al., issued Sep. 8, 1990.

It should also be noted, however, that none of the patents referenced hereinabove teach, claim or even suggest utilizing multiple light sources, positioned at different angles and operated one at a time in sequence, to extend the angular scatter measurement range of an optical scattering particle size analyzer which is the subject of the present invention.

SUMMARY OF THE INVENTION

Accordingly, it is a general object of the invention to provide methods and apparatus for extending the angular measurement range of optical particle size analyzers in a cost effective and reliable manner.

It is a more specific object of the invention to provide methods and apparatus for extending the angular measurement range of optical particle size analyzers in a manner that does not require the use of any more than one collector lens and photodetector array.

Furthermore, it is an object of the invention to provide methods and apparatus for extending the angular measurement range of optical particle size analyzers that use multiple collector lens/detector array sets, without having to add off-axis collector lens/photodetector array combinations.

Still further, it is an object of the invention to provide methods and apparatus, for measuring the size distribution of small particles, that minimize the necessity to align, calibrate and match collector lens/photodetector array sets that could be used to create an extended scatter pattern.

Further yet, it is an object of the invention to provide methods and apparatus which perform the data collection tasks associated with measuring the size distribution of small particles more rapidly than light frequency measurement techniques, especially when particles above approximately 0.1 micron in diameter are being measured.

According to one aspect of the invention, a method (and corresponding apparatus) for determining the size distribution of small particles within a dispersing medium (i.e., for example, a liquid or gas in which the particles are suspended), utilizing a particle analyzer that measures the angle of scattered light, comprises the steps of: (a) sequentially irradiating the particles within the dispersing medium with each of a plurality of light sources positioned at different angles (i.e., operating each of the plurality of light sources one at a time in sequence); (b) focusing the scattered light developed by sequentially irradiating the particles with each of the plurality of light sources, utilizing at least one collector lens, onto a detector array associated with each such lens; (c) sequentially measuring, utilizing each detector array associated with a given lens, the angular distribution of scattered light associated with each of the plurality of light sources; and (d) translating the measured angular distributions of scattered light associated with the plurality of light sources into a size distribution for the particle ensemble contained in the dispersing medium.

According to this first aspect of the invention, the step of sequentially measuring further comprises the steps of: (a) time sharing each detector array among the plurality of light sources, and (b) converting an analog signal developed by each detector array element into a digital signal.

All of the digital signals are input to a programmable digital computing device (such as a commercially available IBM compatible personal computer), which is used to combine the measured angular distributions of scattered light associated with the plurality of light sources into a single angular distribution of scattered light. This single angular distribution of scattered light may then be inverted to obtain said desired size distribution.

Furthermore, according to a preferred embodiment of the invention, well known software implementable mathematical inversion algorithms, such as deconvolution, may be used to ascertain the size distribution from the aforementioned single angular distribution of scattered light.

It should be noted, as will be appreciated by those skilled in the art, that since particle size distribution in a scattering medium is stable with time, different portions of the angular scatter range can be measured sequentially by utilizing a multibeam technique of the type contemplated by the invention and described hereinabove.

According to a further aspect of the invention, a method for extending the angular scatter measurement range of a particle size analyzer that uses a single light source to irradiate particles contained in a dispersing medium to determine the size distribution of the particles, comprises the steps of: (a) utilizing at least one additional light source to irradiate the particles in the dispersing medium, wherein the resulting plurality of light sources are positioned at different angles and are operated sequentially; (b) focusing the scattered light developed by sequentially irradiating the particles with each of the resulting plurality of light sources, utilizing at least one collector lens, onto a detector array associated with each such lens; (c) sequentially measuring, utilizing each detector array associated with a given lens, the angular distribution of scattered light associated with each of the resulting plurality of light sources; and (d) translating the measured angular distributions of scattered light associated with the resulting plurality of light sources into a size distribution for the particle ensemble contained in the dispersing medium.

As in the method for determining the size distribution of small particles within a scattering medium, the method for extending the angular scatter measurement range of a particle size analyzer utilizes a plurality of light sources (the original light source plus the aforementioned additional light sources) to sequentially irradiate the medium at different angles before performing the other processing steps indicated hereinabove.

By using the method for extending the angular scatter measurement range of a particle size analyzer contemplated herein, existing particle analyzers that employ angular scattered light measurement techniques may be upgraded to feature an enhanced angular scattered light measurement range.

The invention also contemplates apparatus which are products of the aforementioned processes.

The invention features the ability to obtain accurate particle size distributions with high resolution. The invention also features the ability to obtain such distributions without having to utilize a multiplicity of expensive collector lens/detector array combinations.

These and other objects, embodiments and features of the present invention and the manner of obtaining them will become apparent to those skilled in the art, and the invention itself will be best understood by reference to the following Detailed Description read in conjunction with the accompanying Drawing.

DETAILED DESCRIPTION

Figure 1:
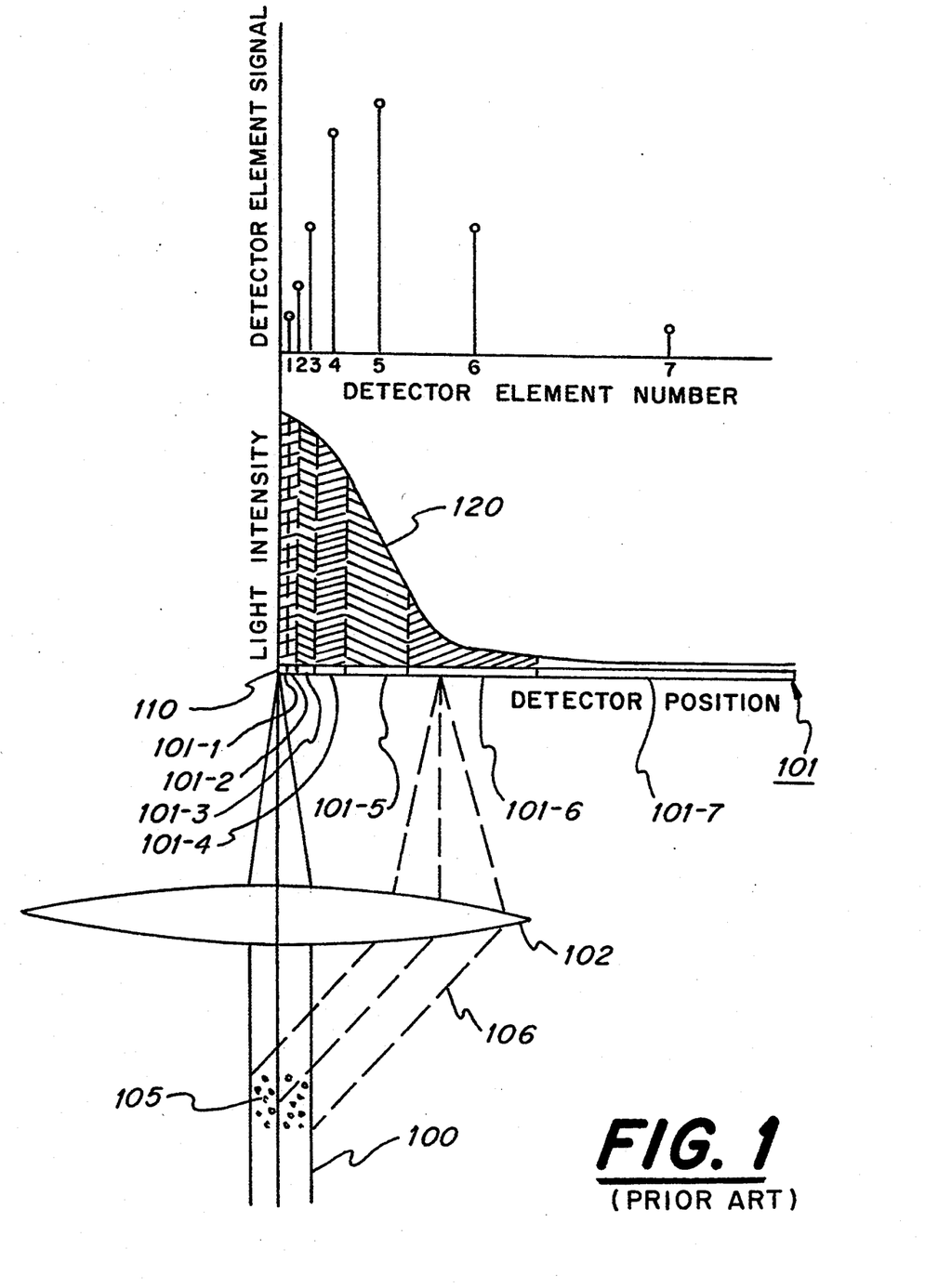
FIG. 1 is an illustration of a prior art technique that uses a detector array, in the focal plane of a collector lens, to generate signals which are each a measure of the total scattered light intercepted by a given detector element in the array.

Although well known by those skilled in the art, a brief description of how a particle size distribution may be obtained by measuring the angular distribution of scattered light will be set forth, for the sake of completeness, with reference to FIG. 1.

FIG. 1, as indicated hereinbefore, is an illustration of a prior art technique that uses a detector array in the focal plane of a collector lens to generate signals which are each a measure of the total scattered light intercepted by a given detector element in the array.

In particular, FIG. 1 depicts light beam 100, incident upon an ensemble of particles, 105 (presumably suspended in a dispersing medium such a liquid or a gas); and how beam 100 is focused onto detector array 101, by collector lens 102, to provide a scattering angle reference of zero degrees for aligning the detector array. The reference is shown as point 110 in FIG. 1.

Furthermore, FIG. 1 depicts scattered light beam 106 being focused by lens 102 onto detector array 101.

For the sake of illustration only, detector array 101 is depicted as a logarithmic line array including illustrative detector elements 101-1 thru 101-7. The structure, function and utility of logarithmic line arrays, for particle measurement purposes, is taught in an article entitled "Particle Size Measurement-Impulse Response Model For Inversion Of Scattered Light", by Trainer et al., published at pp 169–177 in the Proceedings of The Second International Congress On Optical Particle Sizing, held Mar. 5–9, 1990. This publication is hereby incorporated by reference.

It will be appreciated by those skilled in the art that the teachings of the invention may be applied in particle measurement systems employing other types of detector array structures, such as linear arrays and annular arrays. However, although not required, the use of a logarithmic line detector array as illustrated in FIG. 1, is considered advantageous in the particle measurement systems contemplated by the invention because (a) use of such an array permits the direct use of deconvolution (which is superior to other inversion techniques), to obtain a particle size distribution, and (b) use of such an array has been determined to improve the resolution of the multibeam particle size analyzers described herein.

The intensity of the light scattered by the particles (scattered light intensity) versus position on the detector array is shown represented by curve 120 in FIG. 1; and the area under each section of curve 120 bounded by a given detector element is represented in FIG. 1 in the plot of detector element signal versus detector element number.

For example, signals 1–7, shown in FIG. 1, represent the signal output from each of detector elements 101-1 thru 101-7, respectively, and thereby represent the areas under the sections of curve 120 bounded by the respective detector elements. Each of these signals may also be thought of as a measure of total scattered light intercepted by a given detector element in a set of detector arrays.

Signals 1–7 in FIG. 1 (representing analog detector array output signals), are typically converted to digital signals (using well known A/D conversion techniques) for further processing to obtain the desired particle size distribution by using well known inversion techniques.

Those skilled in the art will recognize that once obtained, the particle size distribution may be used to determine the total volume, area or number of particles in a predetermined size range.

Figure 2:
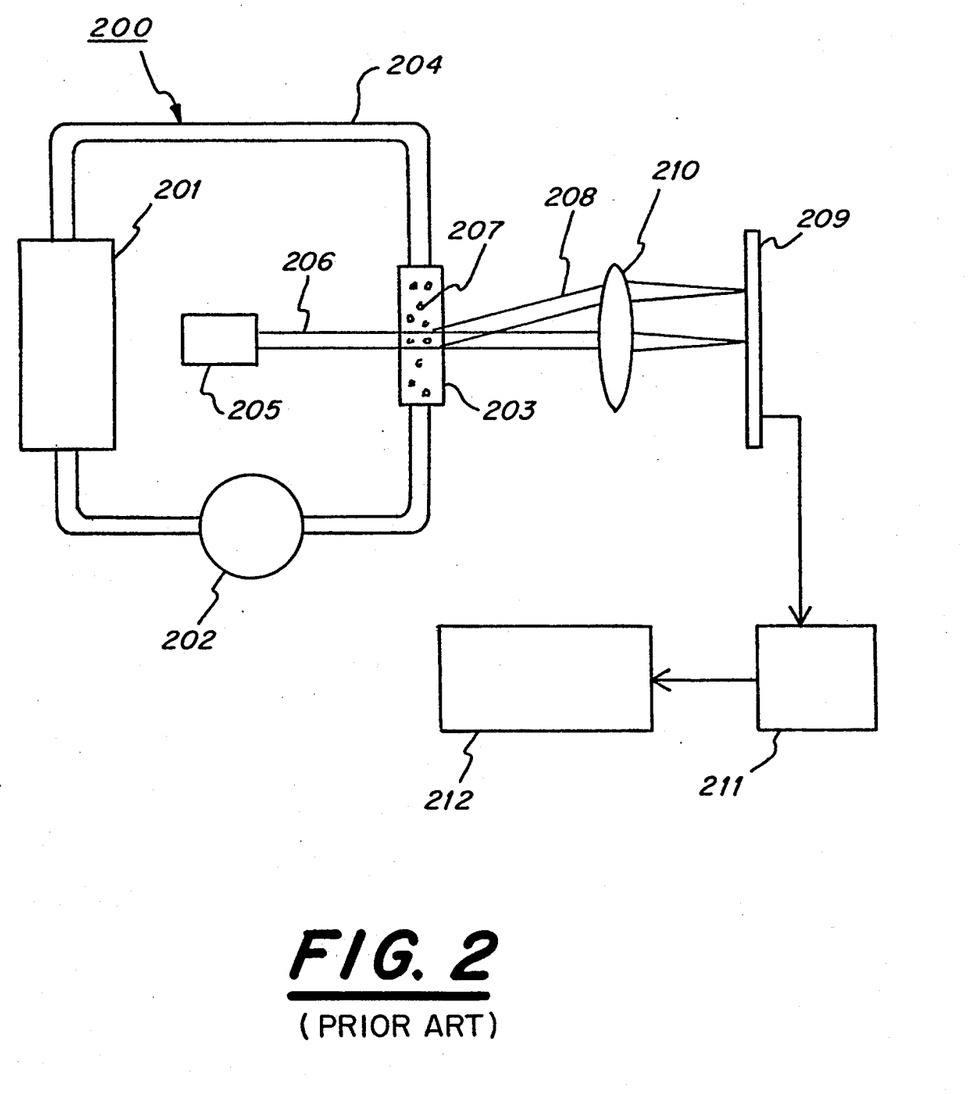
FIG. 2 depicts, in the form of a block diagram, a prior art device for determining a particle size distribution over a limited scattering angle range, where the device utilizes a single collector lens/detector array set to develop measurement signals of the type depicted in FIG. 1.

Having described how a particle size distribution may be obtained by measuring the angular distribution of scattered light, reference should now be made to FIG. 2 which depicts, in the form of a block diagram, a prior art device for determining a particle size distribution over a limited scattering angle range. The device depicted in FIG. 2 utilizes a single collector lens/detector array set to develop measurement signals of the type described with reference to FIG. 1.

The type of device depicted in FIG. 2 is commercially available in the form of the aforementioned SRA. The components of the device depicted in FIG. 2 will be described hereinafter in order to indicate (with reference to FIG. 4) how such a device may be modified, in accordance with the teachings of the invention, to extend its angular range.

The particle analyzer shown in FIG. 2 includes a sample system 200, that further includes a sample reservoir 201, sample pump 202 and sample cell 203; all interconnected via tubing 204. Particles being measured are typically suspended in a dispersing medium contained in sample system 200.

The device depicted in FIG. 2 is also shown to include light source 205 (preferably collimated like the laser source used in the SRA system), which generates light beam 206 shown passing through sample cell 203 containing particle ensemble 207. Incident light beam 206 and scattered light beam 208 are shown focused on detector array 209 via a single collector lens, 210.

The detector element signals, (which are shown in FIG. 1 as exemplary signals 1–7), are converted from analog form to digital form by A/D converter 211; and are subsequently processed, by programmable digital computing device 212 (in the manner described hereinbefore before with reference to FIG. 1), to obtain the particle size distribution for particle ensemble 207.

Figure 3:
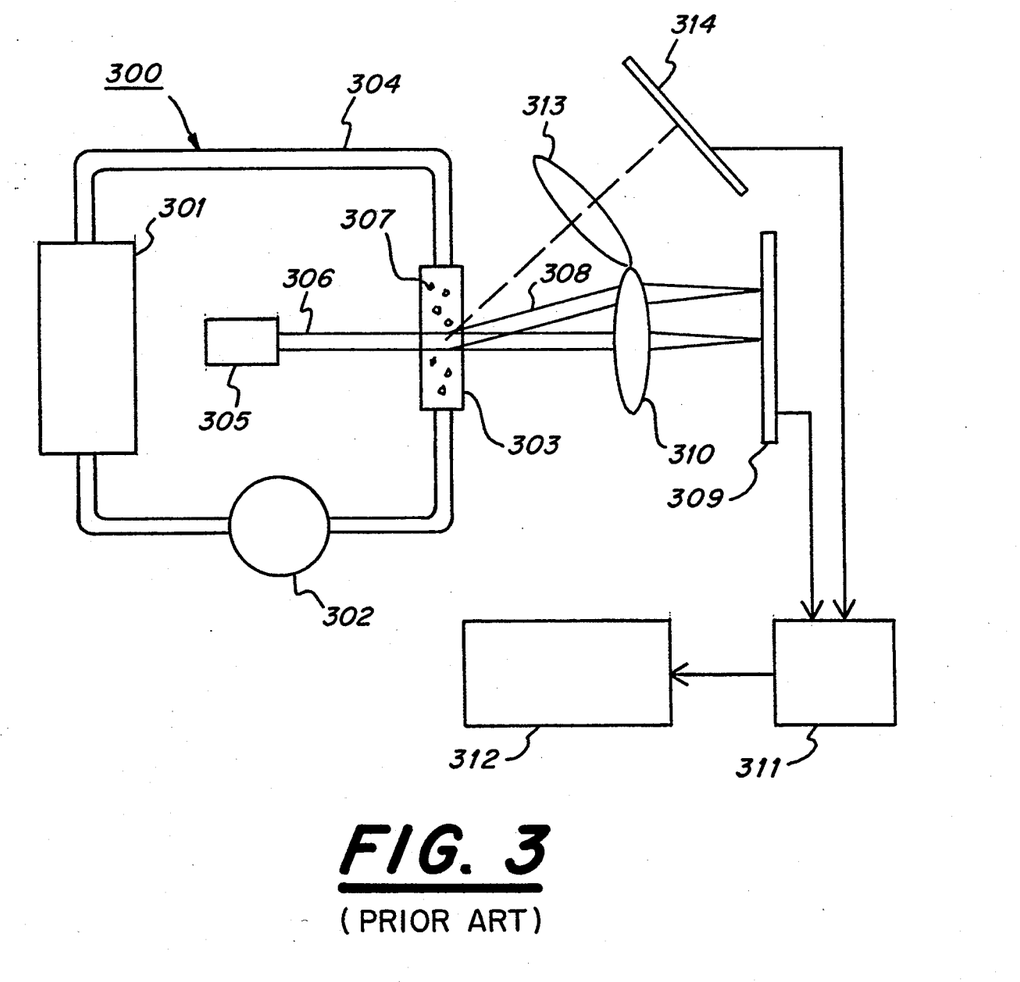
FIG. 3 depicts, in the form of a block diagram, a prior art device for determining a particle size distribution over a wider scattering angle range then the device depicted in FIG. 2, where the device depicted in FIG. 3 utilizes multiple collector lens/detector array sets to each develop measurement signals of the type depicted in FIG. 1.

Reference should now be made to FIG. 3 which depicts, in the form of a block diagram, a prior art device for determining a particle size distribution over a wider scattering angle range then the device depicted in FIG. 2. The device depicted in FIG. 3 utilizes multiple collector lens/detector array sets to each develop measurement signals of the type depicted in FIG. 1.

The type of device depicted in FIG. 3 is commercially available in the form of the aforementioned FRA. The components of the device depicted in FIG. 3 will be described hereinafter in order to indicate (with reference to FIG. 5) how such a device may be modified, in accordance with the teachings of the invention, to extend its angular range.

The particle analyzer shown in FIG. 3 includes elements 300–312 which correspond to elements 200–212, respectively, shown in FIG. 2 and previously described herein.

Furthermore, the device shown in FIG. 3 is shown to include off-axis collector lens 313 and detector array, 314 (associated with lens 313); used in combination to extend the angular range of the FRA (when compared to the SRA).

Figure 4:
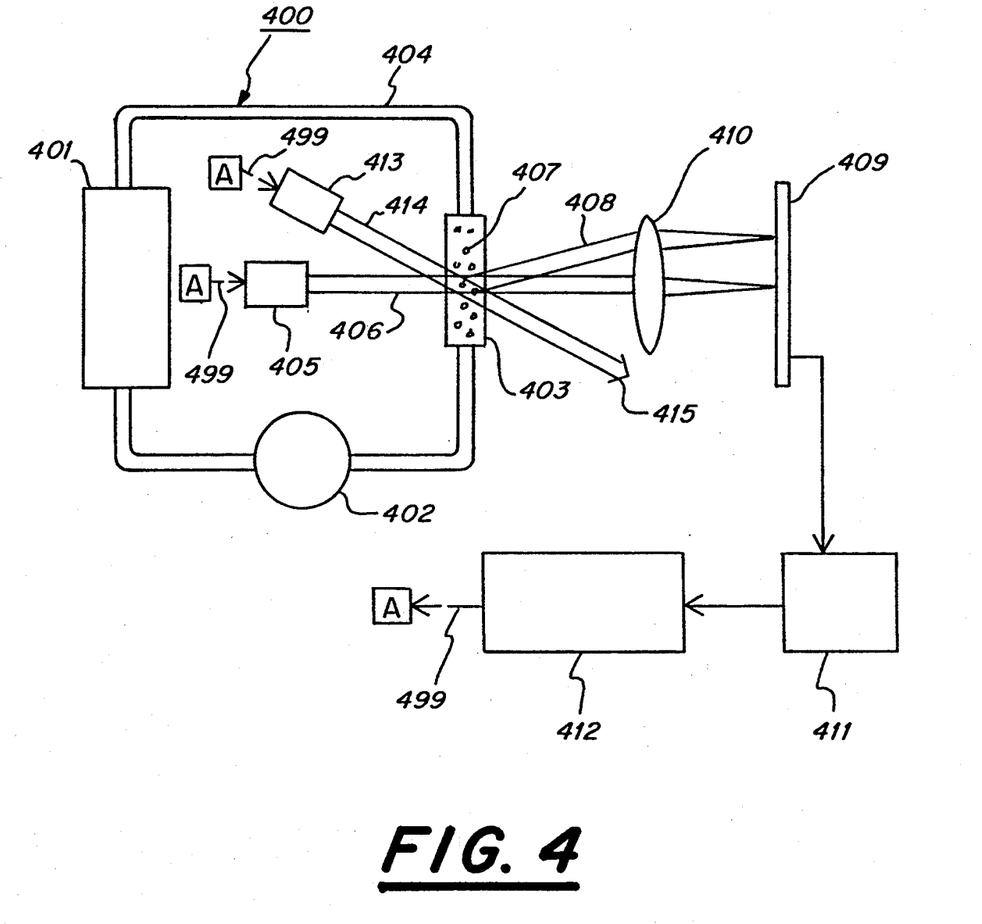
FIG. 4 depicts, in the form of a block diagram, exemplary apparatus which, in accordance with the teachings of the invention, may be used for determining small particle size distribution utilizing multiple light beams to extend the angular scatter measurement range of a device, like the particle analyzer depicted in FIG. 2.

Reference should now be made to FIG. 4 which depicts, in the form of a block diagram, exemplary apparatus that, in accordance with the teachings of the invention, may be used for determining small particle size distribution utilizing multiple light beams to extend the angular scatter measurement range of a device, like the particle analyzer depicted in FIG. 2.

In particular, FIG. 4 includes elements 400–412 which correspond to elements 200–212, respectively, shown in FIG. 2 and previously described herein.

In addition, the device depicted in FIG. 4 is shown to include a second light source, 413; which produces incident light beam 414 that is preferably captured by beam dump 415.

According to the invention, light sources 405 and 413 are positioned at different angles (relative to collector lens 410), so that two different ranges of angular scatter can be measured using detector array 409 on a time shared basis.

The time sharing of detector array 409 may, for example, be accomplished by programming computer 412 to switch light sources 405 and 413 on in sequence (i.e, only one light source is on at a given time), for a preselected time period, thereby sequentially irradiating the particles with beams having different angles with respect to collector lens 410 (effectively extending the range of scattering angles intercepted by collector lens 410). An exemplary means for enabling computer 412 to control the switching of light sources 405 and 413, is shown in FIG. 4 as control link 499.

Furthermore, according to the invention, the measured angular distributions of scattered light obtained by utilizing the device depicted in FIG. 4 (where the distributions are associated with the two depicted light sources 405 and 413), are translated into a size distribution for particle ensemble 407, using computer 412.

According to a preferred embodiment of the invention, the translating process includes the steps of combining the measured angular distributions of scattered light associated with the two (or any plurality of) light sources into a single angular distribution of scattered light; and inverting said single angular distribution of scattered light to obtain the desired size distribution.

As indicated hereinbefore the aforementioned step of inverting may be performed by deconvolving the aforementioned single angular distribution of scattered light.

Those skilled in the art will readily appreciate that the description of the invention set forth with reference to FIG. 4 has been presented for the sake of illustration only and that, for example, a greater number of light sources and/or collector lens/detector array combinations could be used without departing from the spirit or scope of the invention.

For the sake of cost effectiveness, the preferable light sources to use in the device depicted in FIG. 4 (and later in FIG. 5), are laser diodes each with a collimating lens.

Figure 5:
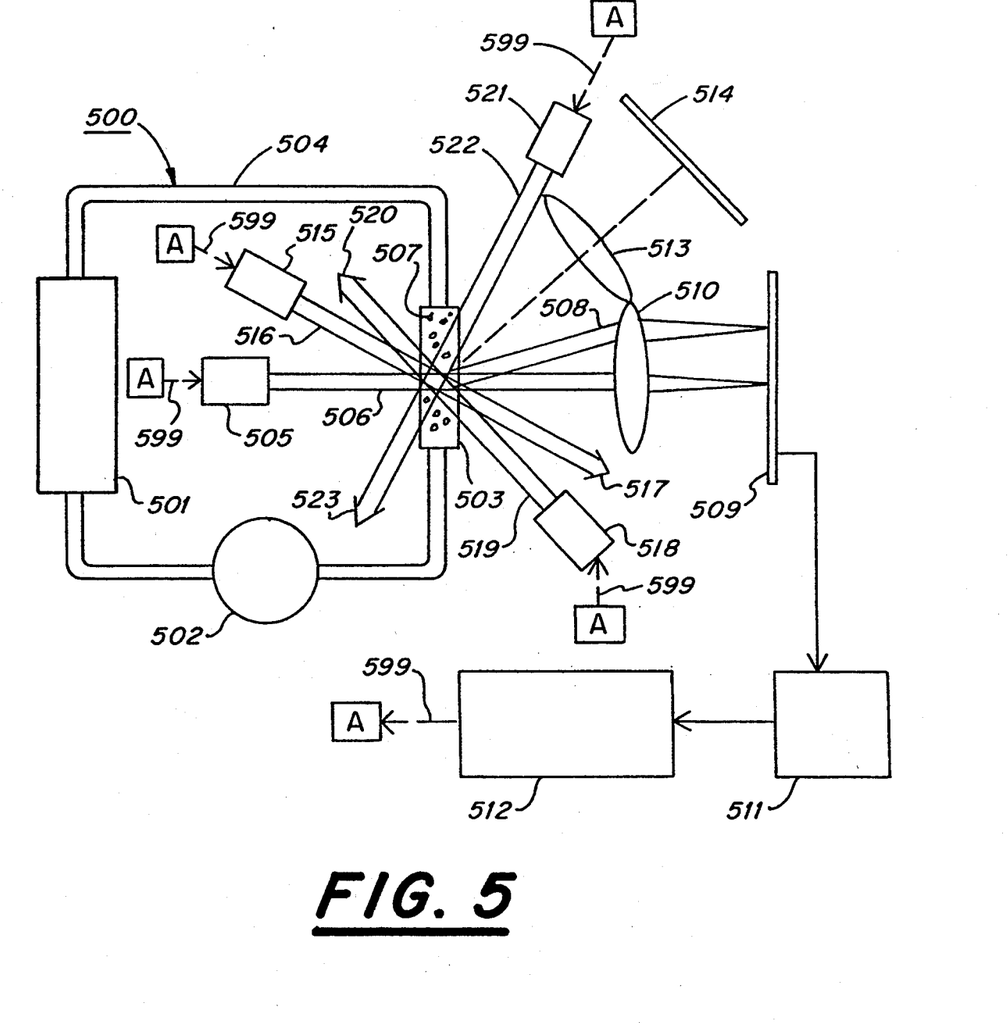
FIG. 5 depicts, in the form of a block diagram, exemplary apparatus which, in accordance with the teachings of the invention, may be used for determining small particle size distribution utilizing multiple light beams to extend the angular scatter measurement range of a device, like the particle analyzer depicted in FIG. 3.

Reference should now be made to FIG. 5 which depicts, in the form of a block diagram, exemplary apparatus that, in accordance with the teachings of the invention, may be used for determining small particle size distribution utilizing multiple light beams to extend the angular scatter measurement range of a device, like the particle analyzer depicted in FIG. 3.

In particular, FIG. 5 includes elements 500–514 which correspond to elements 300–314, respectively, shown in FIG. 3 and previously described herein.

In addition, the device depicted in FIG. 5 is shown to include a second, third and fourth light source (sources 515, 518 and 521); which respectively produce incident light beam 516, 519 and 522; preferably captured, respectively, by beam dumps 517, 520 and 523.

According to the invention, light sources 505, 515, 518 and 521 are positioned at different angles (relative to collector lenses 510 and 513), so that four different ranges of angular scatter (one for each source) can be measured using detector arrays 509 and 514 on a time shared basis. Those skilled in the art will readily appreciate that the light source angles should be selected to avoid high light reflection from the sample cell.

The time sharing of detector arrays 509 and 514 may be accomplished by programming computer 512 to switch light sources 505, 515, 518 and 521 on in sequence (i.e, only one light source is on at a given time), for a preselected time period, thereby sequentially irradiating the particles with beams having different angles with respect to collector lenses 510 and 513 (effectively extending the range of scattering angles intercepted by collector lenses 510 and 513). An exemplary means for enabling computer 412 to control the switching of light sources 505, 515, 518 and 521, is shown in FIG. 5 as control link 599.

Furthermore, according to the invention, the measured angular distributions of scattered light obtained by utilizing the device depicted in FIG. 5 (where the distributions are associated with the four depicted light sources 505, 515, 518 and 521), are translated into a size distribution for particle ensemble 507, using computer 512.

According to a preferred embodiment of the invention, the translating process includes the steps of combining the measured angular distributions of scattered light associated with the four (or any plurality of) light sources into a single angular distribution of scattered light; and inverting said single angular distribution of scattered light to obtain the desired size distribution.

As indicated hereinbefore the aforementioned step of inverting may be performed by deconvolving the aforementioned single angular distribution of scattered light.

It should be noted that, according to a preferred embodiment of the invention, the lens, array and electronics sets depicted in FIG. 4 and FIG. 5 may utilize common calibration and alignment devices. The intensities of the light sources are used to normalize the scatter data from each light source. Alternatively, the aforementioned normalization process could be performed by using overlapping ranges of scattering angle (as may be seen hereinafter with reference to FIG. 6B).

Those skilled in the art will readily appreciate that by using the teachings of the invention the devices depicted in FIG. 4 and FIG. 5 could also be used to create a continuous scatter pattern measurement over the entire available angular range of from 0 to 180 degrees. The analysis of the full angular range allows particle size to be determined to sizes less than 0.1 micron.

Those skilled in the art will readily appreciate that the description of the invention set forth with reference to FIG. 5 has been presented for the sake of illustration only and that, for example, a greater number of light sources and/or collector lens/detector array combinations could be used without departing from the spirit or scope of the invention.

It should be noted that the devices depicted in FIGS. 4 and 5 are operative to determine the size distribution of small particles within a dispersing medium by sequentially irradiating the particles within the medium with each of a plurality of light sources positioned at different angles. Thus, in addition to being able to extend the angular scatter measurement range of existing devices (using the techniques described hereinbefore with reference to FIGS. 2-5), it can be seen that a key aspect of the invention is directed to particle analyzers per se (whether extended or not), which employ the multibeam measurement techniques taught herein.

Figure 6A:
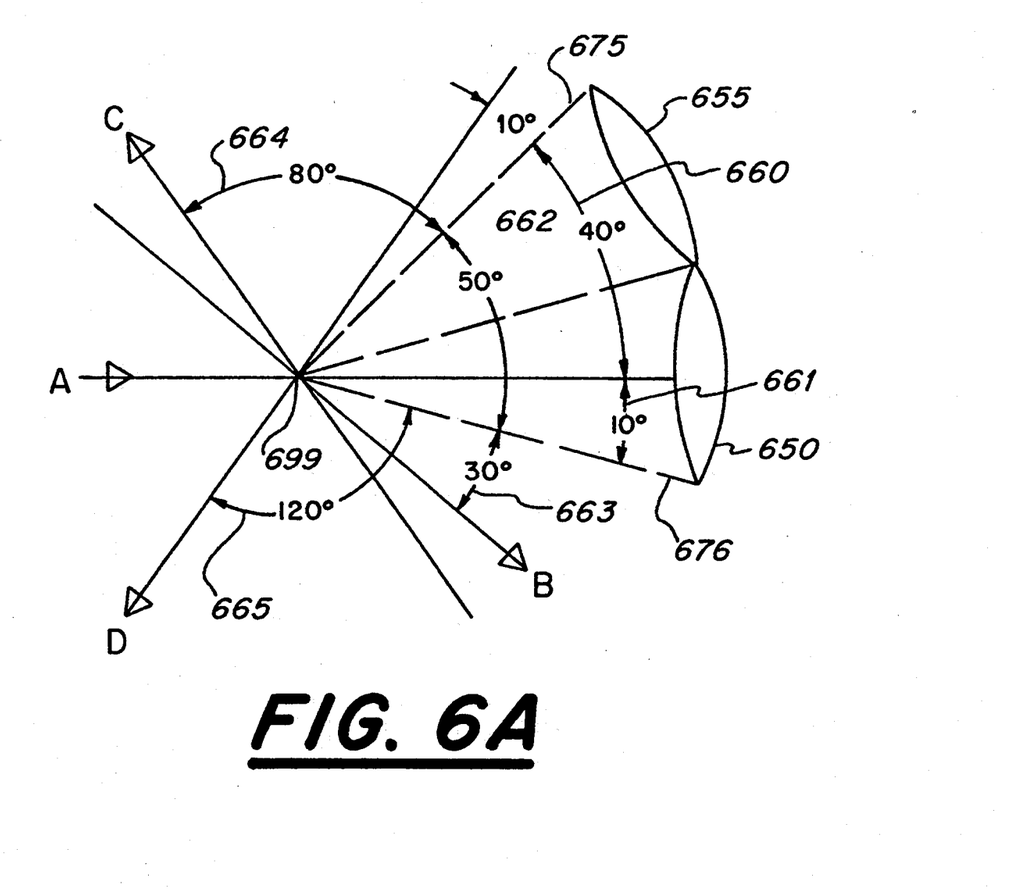
FIG. 6A and FIG. 6B depict a quantitative example of how the multiple light sources depicted in FIG. 5 may be used to cover an angular scattered light measurement range of 170 degrees.
Figure 6B:
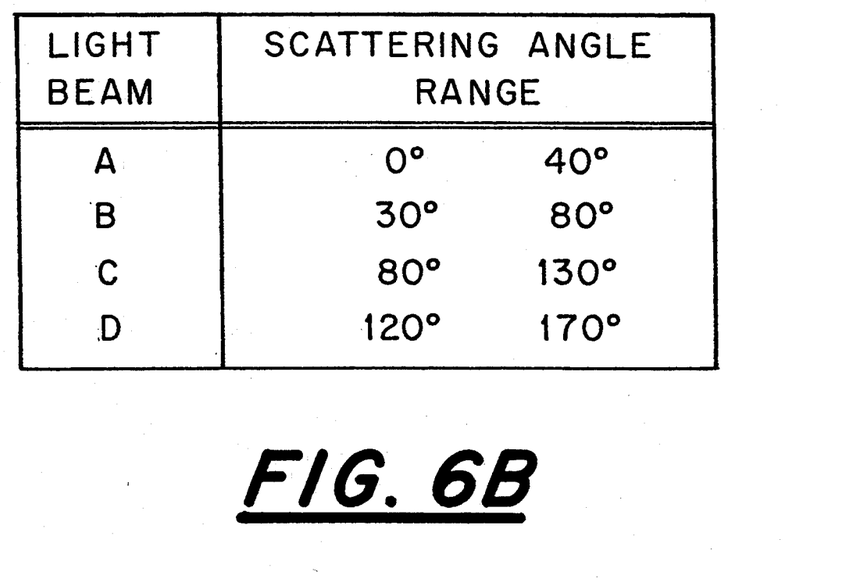

Reference should now be made to FIG. 6A and FIG. 6B which, as indicated hereinbefore, depict a quantitative example of how the multiple light sources depicted in FIG. 5 may be used to cover an angular scattered light measurement range of 170 degrees.

In particular, FIG. 6A illustrates that a particle analyzer configuration with 4 light beams generated by 4 separate sources (such as the device depicted in FIG. 5), can be used to cover almost all of the entire 180 degree scattering range. As those skilled in the art will readily appreciate, the angular scattering distribution is symmetrical about the incident light source direction, and accordingly only half of the full 360 degree range is needed to measure all possible scattering angles.

Each of the four light beams depicted in FIG. 6A, light beams A through D, cover a different portion of the illustrative angular scattered light measurement range of 170 degrees. The full 170 degree angular range is measured by sequentially turning one light source on at a time.

In particular, as may be seen with reference to both FIG. 6A and the table shown in FIG. 6B, light beam A is directed through particle ensemble 699. Light beam A is illustrated as covering the scattering angle range between 0 and 40 degrees, relative to the direction of beam A, by arc 660. It should be noted that the 10 degrees of scattering angle range shown by arc 661, relative to the direction of beam A, is by virtue of the aforementioned symmetry included in arc 660.

Light beam B in FIG. 6A is illustrated as covering the scattering angle range between 30 degrees and 80 degrees, relative to the direction of beam B, by arcs 662 and 663. This 50 degree range corresponds to the full angular range of illustrative collector lenses 650 and 655.

Light beam C in FIG. 6A is illustrated as covering the scattering angle range between 80 degrees and 130 degrees, relative to the direction of beam C, by arcs 662 and 664. It should be noted that the 80 degree arc 664 corresponds to the minimum angle between beam C and the limits of the combined angular range of illustrative lenses 650 and 655, indicated by dashed lines 675 and 676. By definition, the minimum angular distance from a given beam to the angular range limits of the depicted lenses (660 and 655), is the minimum component of the range defined for the given beam.

Light beam D in FIG. 6A is illustrated as covering the scattering angle range between 120 degrees and 170 degrees, relative to the direction of beam D, by arcs 665 and 662. This 50 degree range corresponds to the full angular range of illustrative collector lenses 650 and 655.

It can be seen with reference to FIGS. 6A and 6B that the minimum and maximum scatter angles for light beams A and B; and C and D, overlap. This illustrative choice of light beam angles may be used to normalize the angular scattering data between the overlapping pairs of light beams. For example, all of the angular scatter data taken from beam B, can be scaled (or normalized) to all of the data from beam A by multiplying the data from beam B by the ratio of the overlapping data from beam A divided by the overlapping data from beam B, which is a constant.

Figure 7:
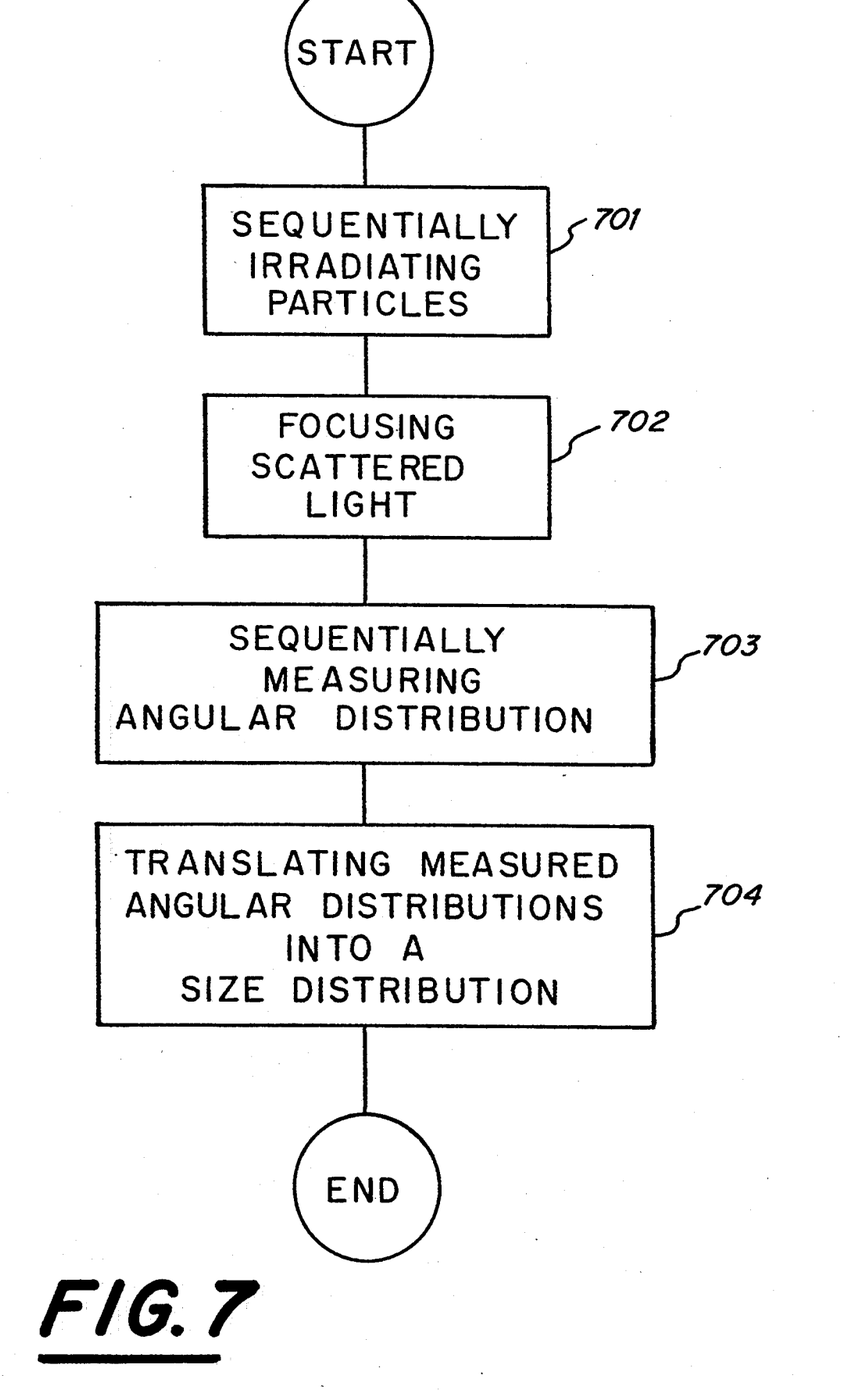
FIG. 7 depicts, in the form of a flowchart, a process contemplated by the invention for determining the size distribution of small particles within a scattering medium utilizing a particle size analyzer that measures the angle of scattered light.

Reference should now be made to FIG. 7 which depicts, in the form of a flowchart, a process contemplated by the invention for determining the size distribution of small particles within a scattering medium utilizing a particle size analyzer that measures the angle of scattered light.

In particular, the exemplary process depicted in FIG. 7 includes the steps of: (a) sequentially irradiating the particles within a dispersing medium with each of a plurality of light sources positioned at different angles (shown at block 701 in FIG. 7 as the step of "Sequentially Irradiating Particles"); (b) focusing the scattered light developed by sequentially irradiating the particles with each of the plurality of light sources, utilizing at least one collector lens, onto a detector array associated with each such lens (shown at block 702 in FIG. 7 as the step of "Focussing Scattered Light"); (c) sequentially measuring, utilizing each detector array associated with a given lens, the angular distribution of scattered light associated with each of the plurality of light sources (shown at block 703 in FIG. 7 as the step of "Sequentially Measuring Angular Distribution"); and (d) translating the measured angular distributions of scattered light associated with the plurality of light sources into a size distribution for the particle ensemble contained in the dispersing medium (shown at block 704 in FIG. 7 as the step of "Translating Measured Angular Distributions Into A Size Distribution").

Figure 8:
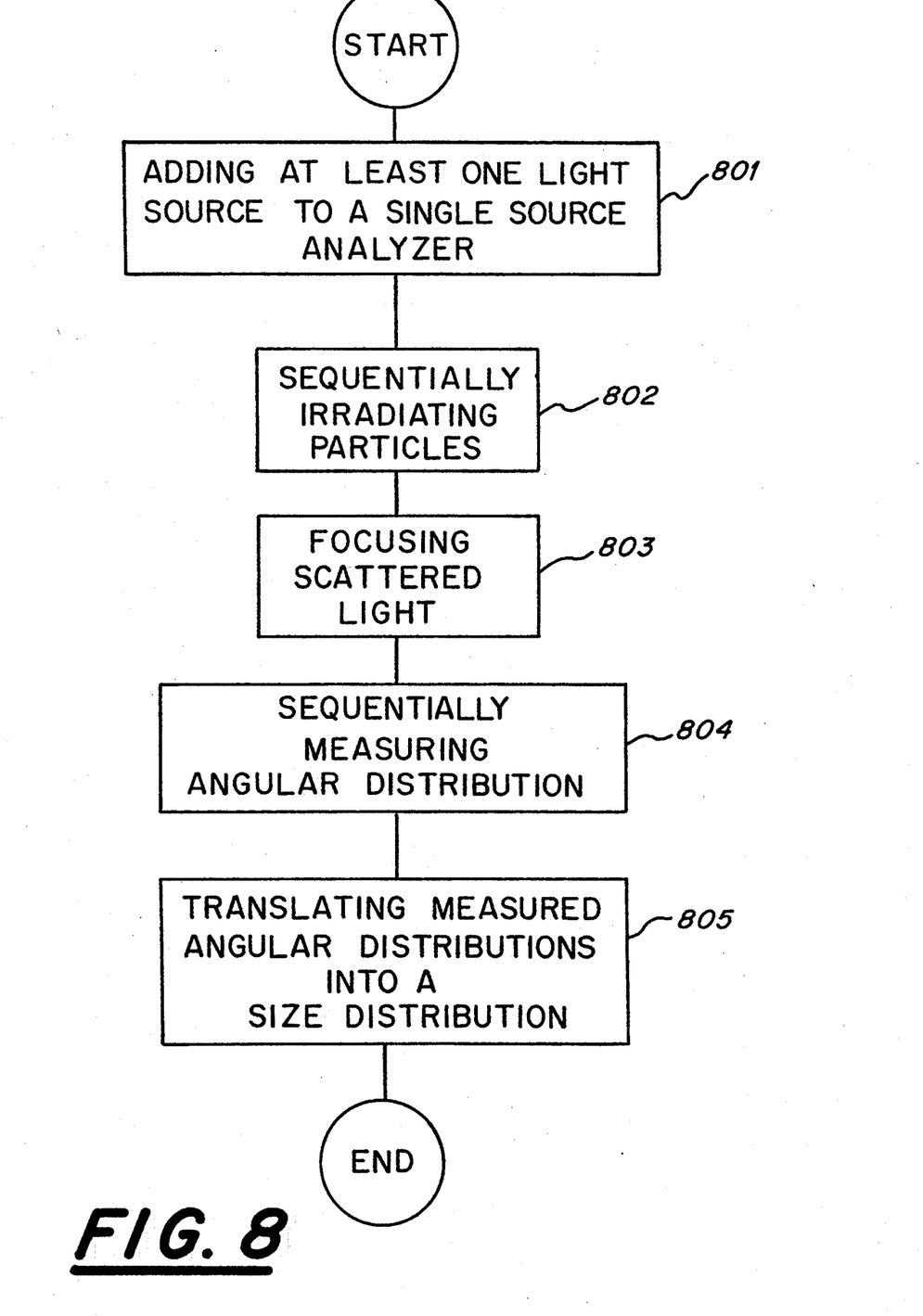
FIG. 8 depicts, in the form of a flowchart, a process contemplated by the invention for extending the angular scatter measurement range of a particle size analyzer that measures the angle of scattered light.

Reference should now be made to FIG. 8 which depicts, in the form of a flowchart, a process contemplated by the invention for extending the angular scatter measurement range of a particle size analyzer that measures the angle of scattered light. It is assumed with reference to the process depicted in FIG. 8 that the given particle analyzer uses a single light source to irradiate particles contained in a dispersing medium to determine the size distribution of the particles.

In particular, the exemplary process depicted in FIG. 8 includes the steps of: (a1) utilizing at least one additional light source (shown at block 801 in FIG. 8 as the step of "Adding At Least One Light Source To A Single Source Analyzer"), to (a2) irradiate the particles in the dispersing medium, wherein the resulting plurality of light sources are positioned at different angles and are operated sequentially (shown at block 802 in FIG. 8 as the step of "Sequentially Irradiating Particles"); (b) focusing the scattered light developed by sequentially irradiating said particles with each of said resulting plurality of light sources, utilizing at least one collector lens, onto a detector array associated with each such lens (shown at block 803 in FIG. 8 as the step of "Focussing Scattered Light"); (c) sequentially measuring, utilizing each detector array associated with a given lens, the angular distribution of scattered light associated with each of said resulting plurality of light sources (shown at block 804 in FIG. 8 as the step of "Sequentially Measuring Angular Distribution"); and (d) translating the measured angular distributions of scattered light associated with said resulting plurality of light sources into a size distribution for the particle ensemble contained in the dispersing medium (shown at block 805 in FIG. 8 as the step of "Translating Measured Angular Distributions Into A Size Distribution").

What has been described in detail hereinabove are methods and apparatus meeting all of the aforestated objectives. As previously indicated, those skilled in the art will recognize that the foregoing description has been presented for the sake of illustration and description only. It is not intended to be exhaustive or to limit the invention to the precise form disclosed, and obviously many modifications and variations are possible in light of the above teaching.

The embodiments and examples set forth herein were presented in order to best explain the principles of the instant invention and its practical application to thereby enable others skilled in the art to best utilize the instant invention in various embodiments and with various modifications as are suited to the particular use contemplated.

It is, therefore, to be understood that the claims appended hereto are intended to cover all such modifications and variations which fall within the true scope and spirit of the invention.

What is claimed is:

1. A method for determining the size distribution of small particles within a dispersing medium utilizing a particle analyzer that measures the angle of scattered light, comprising the steps of:
    (a) sequentially irradiating the particles within said dispersing medium with each of a plurality of light sources positioned at different angles;
    (b) focusing the scattered light developed by sequentially irradiating said particles with each of said plurality of light sources, utilizing at least one collector lens, onto a detector array associated with each such lens, wherein each such detector array is located in the focal .plane of the lens associated therewith;
    (c) sequentially measuring, utilizing each detector array associated with a given lens, the angular distribution of scattered light associated with each of said plurality of light sources; and
    (d) translating the measured angular distributions of scattered light associated with said plurality of light sources into a size distribution for the particle ensemble contained in the dispersing medium.

2. A method as set forth in claim 1 wherein said step of sequentially irradiating is performed utilizing at least one light source which is a laser.

3. A method as set forth in claim 1 wherein said step of sequentially measuring is performed utilizing at least one detector array that is a logarithmic line array.

4. A method as set forth in claim 1 wherein said step of sequentially measuring further comprises the step of converting an analog signal developed by each detector array element into a digital signal.

5. A method as set forth in claim 1 wherein said step of sequentially measuring further comprises the step of time sharing each detector array among said plurality of light sources.

6. A method as set forth in claim 1 wherein said step of translating further comprises the steps of:
    (a) combining the measured angular distributions of scattered light associated with said plurality of light sources into a single angular distribution of scattered light; and
    (b) inverting said single angular distribution of scattered light to obtain said size distribution.

7. A method as set forth in claim 6 wherein said step of inverting is performed by deconvolving said single angular distribution of scattered light.

8. A method for extending the angular scatter measurement range of a particle size analyzer that uses a single light source to irradiate particles contained in a dispersing medium to determine the size distribution of said particles, comprising the steps of:
    (a) utilizing at least one additional light source to irradiate the particles in said dispersing medium, wherein the resulting plurality of light sources are positioned at different angles and are operated sequentially;

(b) focusing the scattered light developed by sequentially irradiating said particles with each of said resulting plurality of light sources, utilizing at least one collector lens, onto a detector array associated with each such lens, wherein each such detector array is located in the focal plane of the lens associated therewith;

(c) sequentially measuring, utilizing each detector array associated with a given lens, the angular distribution of scattered light associated with each of said resulting plurality of light sources; and (d) translating the measured angular distributions of scattered light associated with said resulting plurality of light sources into a size distribution for the particle ensemble contained in the dispersing medium.

9. A method as set forth in claim 8 wherein said resulting plurality of light sources includes at least one light source which is a laser.

10. A method as set forth in claim 8 wherein said step of sequentially measuring is performed utilizing at least one detector array that is a logarithmic line array.

11. A method as set forth in claim 8 wherein said step of sequentially measuring further comprises the step of converting an analog signal developed by each detector array element into a digital signal.

12. A method as set forth in claim 8 wherein said step of sequentially measuring further comprises the step of time sharing each detector array among said resulting plurality of light sources.

13. A method as set forth in claim 8 wherein said step of translating further comprises the steps of:

(a) combining the measured angular distributions of scattered light associated with said resulting plurality of light sources into a single angular distribution of scattered light; and (b) inverting said single angular distribution of scattered light to obtain said size distribution.

14. A method as set forth in claim 13 wherein said step of inverting is performed by deconvolving said single angular distribution of scattered light.

15. A particle size analyzer which determines the size distribution of small particles within a dispersing medium by measuring the angular distribution of scattered light that results when said particles are irradiated, comprising:

(a) a plurality of light sources positioned at different angles;

(b) means for sequentially irradiating the particles within said dispersing medium with each of said plurality of light sources;

(c) at least one means for focusing the scattered light developed by sequentially irradiating said particles with each of said plurality of light sources, onto a detector array associated with each of said means for focusing, wherein each such detector array is located in the focal plane of the means for focusing associated therewith;

(d) means for sequentially measuring, utilizing each detector array associated with a given means for focusing, the angular distribution of scattered light associated with each of said plurality of light sources; and (e) means for translating the measured angular distributions of scattered light associated with said plurality of light sources into a size distribution for the particle ensemble contained in the dispersing medium.

16. Apparatus as set forth in claim 15 wherein each of said at least one means for focusing is a collector lens.

17. Apparatus as set forth in claim 15 wherein said means for translating is a programmable digital computer.

18. Apparatus as set forth in claim 15 wherein at least one of said plurality of light sources is a laser.

19. Apparatus as set forth in claim 15 wherein at least one detector array associated with a given means for focusing is a logarithmic line array.

20. Apparatus as set forth in claim 15 wherein said means for sequentially measuring further comprises an analog to digital converter.

21. Apparatus for extending the angular scatter measurement range of a particle size analyzer that uses a single light source to irradiate particles contained in a dispersing medium to determine the size distribution of said particles, comprising:

(a) at least one additional light source to irradiate the particles in said dispersing medium, wherein the resulting plurality of light sources are positioned at different angles and are operated sequentially;

(b) means for focusing, including at least one collector lens, the scattered light developed by sequentially irradiating said particles with each of said resulting plurality of light sources, onto a detector array associated with each such lens, wherein each such detector array is located in the focal plane of the lens associated therewith;

(c) means for sequentially measuring, including each detector array associated with a given lens, the angular distribution of scattered light associated with each of said resulting plurality of light sources; and (d) means for translating the measured angular distributions of scattered light associated with said resulting plurality of light sources into a size distribution for the particle ensemble contained in the dispersing medium.

* * * * *